(12) United States Patent
Driemel

(10) Patent No.: US 9,804,237 B2
(45) Date of Patent: Oct. 31, 2017

(54) BODY COIL FOR MAGNETIC RESONANCE IMAGING

(71) Applicant: Daniel Driemel, Oederan (DE)

(72) Inventor: Daniel Driemel, Oederan (DE)

(73) Assignee: Siemens Aktiengesellschaft, München (DE)

( * ) Notice: Subject to any disclaimer, the term of this patent is extended or adjusted under 35 U.S.C. 154(b) by 356 days.

(21) Appl. No.: 13/763,704

(22) Filed: Feb. 10, 2013

(65) Prior Publication Data

US 2013/0211237 A1 Aug. 15, 2013

(30) Foreign Application Priority Data

Feb. 10, 2012 (DE) .................. 10 2012 202 062

(51) Int. Cl.
| | |
|---|---|
| *A61B 5/05* | (2006.01) |
| *G01R 33/341* | (2006.01) |
| *A61B 5/055* | (2006.01) |
| *A61B 5/00* | (2006.01) |
| *G01R 33/34* | (2006.01) |
| *G01R 33/3415* | (2006.01) |

(52) U.S. Cl.
CPC .......... *G01R 33/341* (2013.01); *A61B 5/0555* (2013.01); *A61B 5/6835* (2013.01); *G01R 33/3415* (2013.01); *G01R 33/34084* (2013.01); *A61B 5/702* (2013.01); *A61B 2562/164* (2013.01)

(58) Field of Classification Search
None
See application file for complete search history.

(56) References Cited

U.S. PATENT DOCUMENTS

| | | | |
|---|---|---|---|
| 7,009,398 B2 | 3/2006 | Hahn et al. | |
| 7,212,002 B2 | 5/2007 | Greim et al. | |
| 7,518,365 B2 | 4/2009 | Driemel | |
| 2005/0012502 A1* | 1/2005 | Renz | 324/318 |
| 2008/0208023 A1* | 8/2008 | Gruvac | A61B 5/14552 600/344 |
| 2009/0027053 A1* | 1/2009 | Decke et al. | 324/318 |

(Continued)

FOREIGN PATENT DOCUMENTS

| | | |
|---|---|---|
| DE | 10 147 743 C1 | 4/2003 |
| DE | 10 2004 006 286 | 10/2004 |

(Continued)

OTHER PUBLICATIONS ("High-Density Polyethylene Foams. I. Polymer and Foam Characterization"; Journal of Applied Polymer Science, 2003, vol. 90, pp. 2111-2119).*

(Continued)

*Primary Examiner* — Amanda Lauritzen Moher
*Assistant Examiner* — Shahdeep Mohammed
(74) *Attorney, Agent, or Firm* — Lempia Summerfield Katz LLC

(57) ABSTRACT

A body coil for magnetic resonance imaging includes one or more coil elements incorporated in a shell material. The body coil has a rectangular basic shape. Two opposing edge sections of the body coil may be pivoted along one pivot axis, respectively, relative to a middle section. For this purpose, movement elements that effect pivoting are arranged on an edge section side.

21 Claims, 4 Drawing Sheets

(56) References Cited

U.S. PATENT DOCUMENTS

2011/0074420 A1 3/2011 Ladebeck
2012/0153956 A1* 6/2012 Driemel ........... G01R 33/34007
                                                    324/322
2012/0161768 A1* 6/2012 Hardy et al. ................. 324/318

FOREIGN PATENT DOCUMENTS

DE   10 2004 005 120       8/2005
DE   10 2006 027 190 A1   12/2007
DE   10 2009 043 446 A1    4/2011

OTHER PUBLICATIONS

German Office Action dated Oct. 12, 2012 for corresponding German Patent Application No. DE 10 2012 202 062.4 with English translation.

* cited by examiner

BODY COIL FOR MAGNETIC RESONANCE IMAGING

This application claims the benefit of DE 10 2012 202 062.4, filed on Feb. 10, 2012, which is hereby incorporated by reference.

BACKGROUND

The present embodiments relate to a body coil including one or more coil elements incorporated in a shell material.

Body coils (e.g., surface coils) are used within the context of magnetic resonance imaging to be able to optimally measure certain regions of the body. To attain a high signal intensity and therewith a high image quality, the body coil may be shaped to the body contour of the patient. For a spinal column coil (e.g., a spine coil), for example, lateral shaping to the patient is desired to increase the image quality in the region of the spine. Known spinal column coils may have a flat construction. The coil is positioned in the examination table so as to be recessed. For this purpose, the examination table has a corresponding upper-side recess, into which the coil is placed. The coil surface, on which the patient is placed, is configured so as to be slightly bent. The middle region is located about 1.5 cm lower than the edge region. Easy shaping to the back contour of the patient is achieved hereby, and the lying comfort is increased. In the case of slim patients who do not require the entire width of the spine coil, the lateral shaping has little effect since the edge regions are ultimately not positioned close to the body. To obtain, for the examination table, a flat surface that is provided, for example, to pull the patient, in the case of unconsciousness, from a stretcher and gurney sideways onto the examination table, the coil-side three-dimensional geometry is such that the body coil does not exceed the upper level of the couch at the side. Otherwise, the coil edge would constitute an obstacle, over which the immobile patient may not be pulled or may only be pulled with difficulty.

SUMMARY AND DESCRIPTION

The present embodiments may obviate one or more of the drawbacks or limitations in the related art. For example, a body coil that offers improved adaptability to the body contour of the patient and may also be optimally integrated in the examination table is provided.

In one embodiment, a body coil includes two opposing edge sections. The edge sections may be pivoted along one pivot axis, respectively, relative to a middle section, for which purpose movement elements that effect pivoting are arranged on an edge section side.

The body coil is constructed in, for example, three parts. The body coil includes a middle section and two lateral edge sections arranged thereon and/or connected thereto so as to be pivotal relative to the middle section. These edge sections may be pivoted about a certain angular dimension, depending on the design of the pivot axis and/or the connection to the middle section, relative to the middle section. In each case, the edge sections may be pivoted such that, with the middle section, the edge sections assume a parallel position that, for example, defines the initial position. From the initial position, the edge sections may be brought into a pivoted-up position adapted to the body contour, so the edge sections assume an optimum position and/or abutment on the patient.

Appropriate movement elements are provided on the edge section side for the purpose of pivoting and undertake pivoting automatically, for example. In other words, the movement elements are functionally designed such that the movement elements bring the edge sections, starting from an initial position (e.g., the above-described initial position, in which the edge sections are substantially parallel to the middle section) into the pivoted-up position applied to the patient. In other words, the coil shape is ultimately not manually adjusted but is ultimately adjusted solely by the action and/or actuation of the movement elements. The specific design of the movement elements is described in more detail below.

A body coil, owing to the possibility of being able to pivot the edge sections into an optimum position relative to the patient body, enables much improved image acquisition since the coil allows shape adjustment close to the body. This adjustment process occurs with the use of the active movement elements that perform the section pivoting, providing that complex manual operations are not required for this. The body coil may also be brought into an initial and basic shape, in which the body coil may be optimally received and/or integrated on the examination table. In other words, the body coil does not protrude beyond the top of the table, so even immobile patients may be brought onto the examination table and/or the body coil without difficulties.

According to a first alternative embodiment, the movement elements may be elastically deformed. The movement elements are therefore capable of establishing a restoring force if the movement elements are deformed, and this restoring force returns the movement elements to the original shape of the movement elements. The movement elements therefore have spring properties to a certain extent.

Different embodiments are provided. According to a first embodiment for pivoting, the movement elements may change volume, starting from a compressed state, to an expanded state. The movement elements are "enlarged," therefore, if the movement elements are relieved of pressure following prior deformation. In the specific case, the coil is positioned on the table. The movement elements are compressed (e.g., deformed), so the coil forms a flat surface (i.e., adopts the initial shape). If the compressed movement elements are relieved of pressure, the compressed movement elements enlarge again, and the inherent restoring force that has built up leads to a change in volume and shape, which effects the movement and pivoting of the edge sections.

Movement elements that change volume may be made from a plastic foam. These are thus foam elements. A visco-foam may be used in this connection. A visco-foam is a memory foam material (e.g., a plastic foam with a "restoring memory"). A shape memory polymer is used for this purpose.

As an alternative to using a plastic foam, for forming the movement elements that change volume, a non-foamed plastics material may be used. In this case, the movement elements may be constructed as hollow bodies. The hollow body has a larger-volume initial shape that is deformable. When the body coil is inserted, this shape, similar to the example described above with the plastic foam movement elements, is likewise deformed until the movement elements are relieved of pressure again. After this, the compressed hollow body enlarges again (i.e., the cavity that contains air and has a ventilation opening expands again), pivoting the edge sections in the process.

The above-described, different variants of the elastically deformable movement elements may have a wedge shape. The wedge shape allows optimum distribution of the compressive force in the direction of the body of the patient.

In the embodiments described above, the movement elements change volume. An alternative embodiment, by contrast, provides that for pivoting, the movement elements change shape, starting from a compressed shape, to an expanded shape. In this case, automatic edge section movement occurs in that the previously compressed movement elements undertake a change in shape. In one embodiment, the movement elements are made from a rubber-elastic plastics material that serves as a spring element. Any desired shape (e.g., a zigzag shape) that is capable of making the movement element act as a spring element and may effect the edge section movement may be used.

An alternative to using an inherent restoring force in the case of the movement elements that establish the deformation provides, by contrast, that the movement elements are constructed as inflatable cushions or balloons. At least one such cushion or at least one such balloon is allocated to each edge section and is inflated with a filling agent (e.g., natural air) via a suitable feed line in addition to a pump and may thus be increased in volume. During inflation, pivoting of the allocated edge section occurs in abutment onto the body contour. Once measuring has ended, the inflated cushions or balloons are relieved of pressure again (i.e., the air is removed therefore, so the edge sections may pivot away again).

The edge sections may be constructed as more or less intrinsically rigid, one-part longitudinal structures. In one embodiment, only one movement element may be allocated to each edge section in this case and, for example, has a similar length to the edge section, so this is actively raised over the entire length, as a plurality of such individual movement elements may also be allocated to such an edge section. However, since the body of the patient does not have a uniform contour, a flexible adjustment is desirable depending on where the body coil is positioned and/or which body section the body coil is examining and is placed on the body coil. To enable this, one embodiment provides that each edge section is intrinsically flexible (i.e., is made from a flexible shell material with flexible coils). In one embodiment, one or more individual movement elements are provided along the respective edge section. The individual movement elements enable a sectoral pivoting of the flexible edge section. As a result, the flexible edge section may be optimally adapted to the corresponding bodily structure because, owing to the flexibility and the individual loading of this section, in regions where the edge section is to be pivoted more, the flexible edge section may be pivoted correspondingly far via a movement element. Other edge sections that are not to be pivoted as far may be similarly optimally positioned.

An alternative provides, that this edge section is divided into a plurality of individual, separately pivotal section elements, to which one movement element, respectively, is allocated. The plurality of individual, separately pivotal section elements may also be rigid. More or less sectoral pivoting and adjustment of the individual section elements occurs here as well. In one embodiment, the section elements may be rigid, although the section elements do not have to be. Even better shape adjustment may be achieved with similarly flexible section elements. This shape adjustment may be provided in the case of the two embodiments described above using any movement element design (e.g., change in volume, change in shape or cushions/balloons). In the case of cushions/balloons, to the cushions/balloons may be inflated separately.

In one embodiment, the plurality of movement elements arranged along an edge section have different elastic properties and/or different shapes. These different degrees of hardness and/or different shapes or thicknesses enable and/or improve optimum shaping in the longitudinal axis of the body.

In one embodiment, pocket-like receptacles for detachably receiving one or more movement elements are provided on the edge sections. The pocket-like receptacles may, for example, be easily introduced into the shell material of the body coil (e.g., a plastics material), but the pocket-like receptacles may also be provided on a separate, flexible part that is secured below the coil edge sections (e.g., glued or molded during the plastic welding process). The detachable arrangement of the movement elements enables the movement elements to be replaced if required. The movement elements may be replaced, for example, in the case of the foam elements following a relatively long period of use In addition to the body coil, an examination table including a top surface component with a rectangular indentation provided on an upper side is provided. At least one body coil of the above-described kind may be inserted into the indentation.

When using the elastic movement elements, the elastic movement elements are deformed and/or compressed in the initial position (e.g., to press the edge sections downwards, the edge sections being automatically pivoted upwards without this action), and the body coil is "leveled." One or more securing devices for securing holding devices provided on the body coil are provided for this purpose on the examination couch component at two opposing edges, and, when secured, hold the edge sections of the body coil by compressing the respective movement elements in a position parallel to the middle section. Counter-support of the movement elements occurs at the base of the indentation, so when the holding devices are connected to the one or more securing devices, edge sections may be pushed downwards.

Hook and loop strips may be used as the holding devices, and corresponding fleece sections, on which the hook and loop strips may catch, are used as the securing devices. Alternatively, corresponding strap-eyelet combinations and the like may also be used.

DETAILED DESCRIPTION OF THE DRAWINGS

Figure 1:
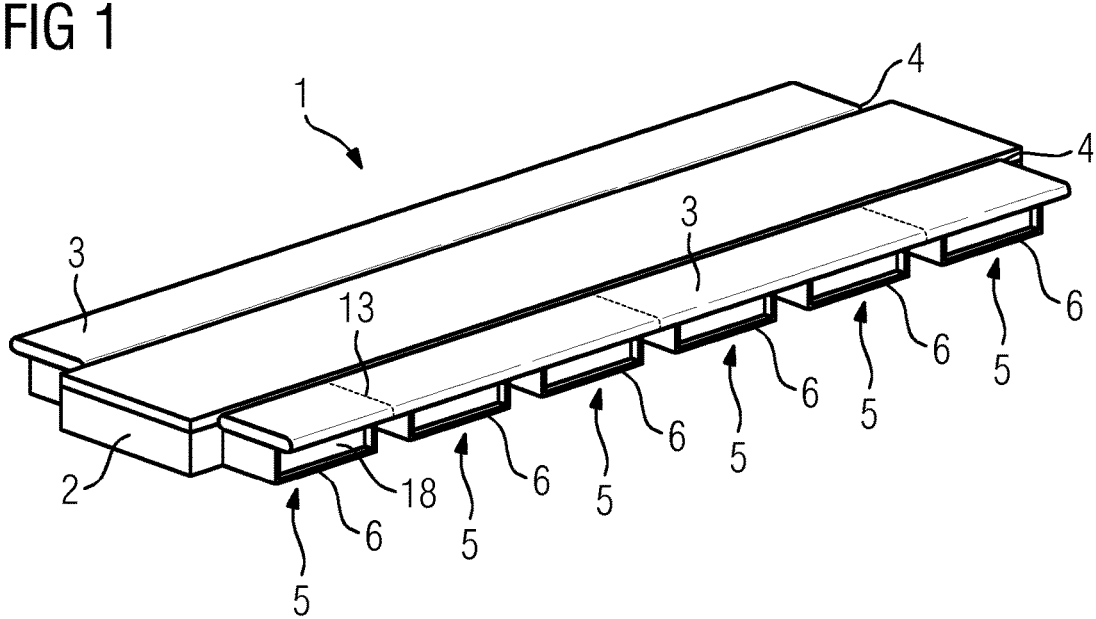
FIG. 1 shows a perspective view of one embodiment of a body coil.

FIG. 1 shows one embodiment of a body coil 1 in the form of a spinal column or spine coil. The body coil 1 includes a rigid middle section 2, relative to which two edge sections 3 may be pivoted. The width of the rigid middle section 2 is designed for the width of a slim patient. Coil elements are received in the middle section 2 and in the edge sections 3 and are surrounded by a suitable shell material. While the shell material in the middle section 2 may be sufficiently rigid, the shell material of the edge sections 3 may, for example, be flexible (e.g., PE foam). This is provided since the edge sections 3 are pivoted upwards in an operating position, as discussed below, in order to optimally adapt to a contour of the patient.

The edge sections 3 may be permanently connected to the middle section 2 by a suitable pivot connection. In one embodiment, the edge sections 3 may be detachably secured to the middle section 2 (e.g., clamped to the middle section). The pivot axis is implemented via an interface, at which the flexible edge sections 3 are joined to the rigid middle section 2. The respective pivot axis 4 runs along the middle section 2, so the edge sections 3 may be pivoted.

In the illustrated example, a plurality of movement elements 5 is allocated to each edge section 3 for this purpose and is provided below the edge section 3. In the illustrated example, the movement elements 5 are received by corresponding pockets 6 that may be shaped directly from the flexible shell material of the edge section (e.g., in PE foam). In one embodiment, on a shared pocket component, the corresponding pockets 6 may be shaped separately from the shared pocket component, which is secured (e.g., glued or thermally joined) below the respective edge section. In each case, any pocket 6 is capable of receiving a movement element 5.

In the illustrated exemplary embodiment, the movement elements 5 are produced in the form of plastic foam elements 18 from plastic foam (e.g., a visco-foam (memory foam material)). The movement elements 5 may therefore be elastically deformed (e.g., brought into an initial state shown in FIG. 1, in which the edge sections 3 are pressed downwards), so a plane extending over the whole body coil 1 is produced. In a relieved state (see FIG. 3), the movement elements 5 have a wedge shape, which is discussed below. In each case, the movement elements 5 are used to automatically pivot the edge sections 3 upwards as soon as the movement elements 5 are relieved of pressure.

Figure 2:
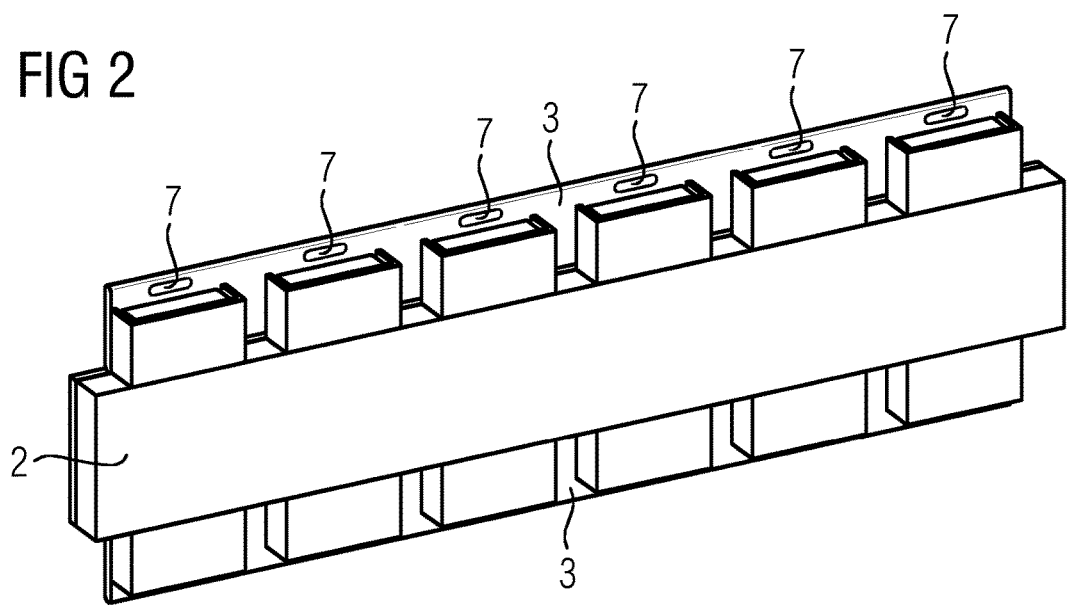
FIG. 2 shows a bottom view of one embodiment of the body coil from FIG. 1.
Figure 5:
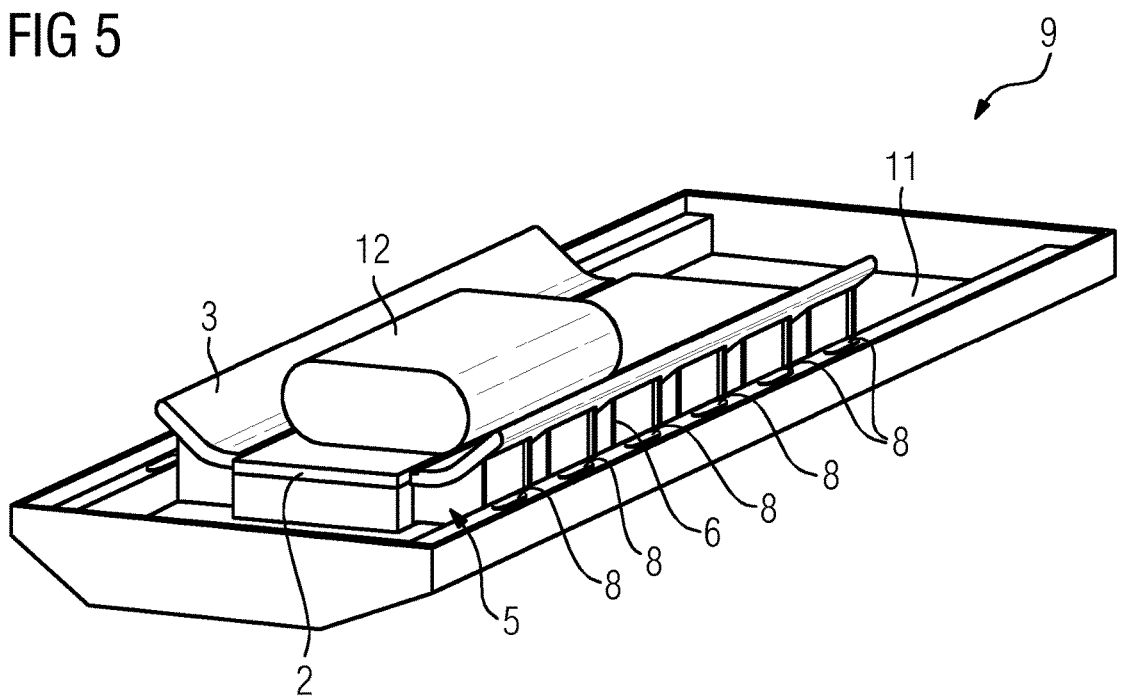
FIG. 5 shows one embodiment of the examination table from FIG. 4 with adjusted body coil.

As shown in FIG. 2, holding devices 7 in the form of hook and loop strips and/or strip sections are arranged on a lower side of each edge section 3. The holding devices 7 (see FIG. 5) cooperate with corresponding securing devices 8 in the form of fleece sections that are arranged on an examination couch component, and fix the edge sections 3 in the downwardly pressed position.

Figure 3:
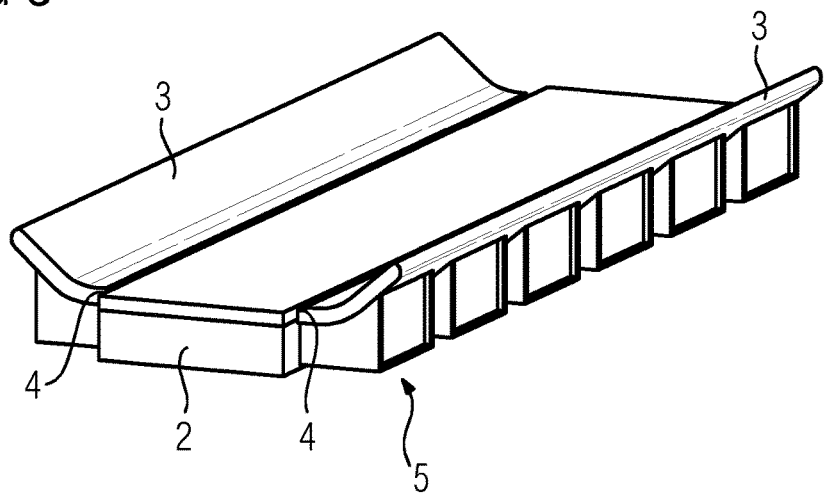
FIG. 3 shows a perspective view of one embodiment of the body coil from FIG. 1 with enlarged movement elements.

FIG. 3 shows the body coil 1 in the "operating position" (e.g., if a patient is lying on the body coil (not shown), and a measurement is to be made). As shown, the movement elements 5 are enlarged, the volume of the movement elements 5 has increased due to being relieved of pressure, and this is a typical property of an elastically compressible plastic foam (e.g., visco-foam). Due to the wedge shape of the movement elements 5, the edge sections 3 are accordingly pivoted upwards about the respective pivot axes 4. The movement elements 5 in the form of the plastic foam wedges 18 may all have the same hardness or elasticity. In one embodiment, the individual movement elements 5 may be configured so as to have different degrees of hardness, and/or the wedge shape may be configured differently, so, in conjunction with the flexibility of the edge sections 3, a locally different adjustment is produced solely by the movement elements 5.

Figure 4:
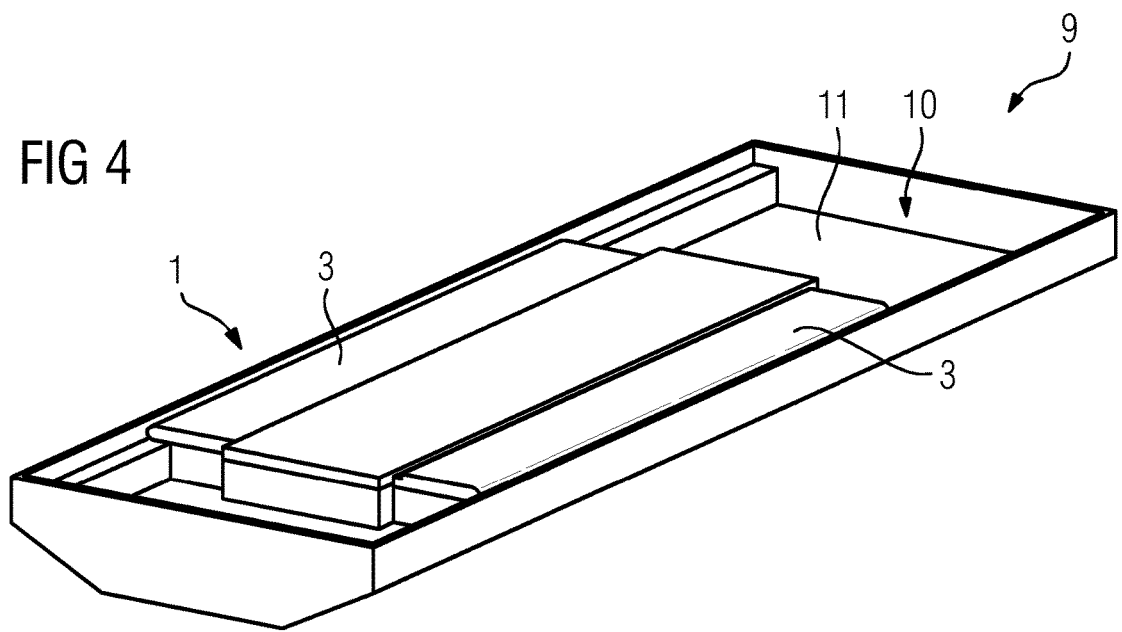
FIG. 4 shows a view of one embodiment of an examination table with inserted body coil in an initial position.

FIG. 4 shows one embodiment of an examination table 9 that includes a central, rectangular recess 10 that matches the shape of the body coil 1. In the illustrated position, the body coil 1 is inserted into the indentation 10, the edge sections 3 are pivoted downwards, where the hook and loop strips 7 adhere to the fleece sections 8, and the edge sections 3 are therefore held down. The edge sections 3 and/or the movement elements 5 in the form of the plastic foam elements 18 are compressed. The plastic foam elements 18 are counter-supported at the base 11 of the indentation 10.

If a patient 12 is now received on the examination table 9, this may be provided since the body coil 1 forms a flat surface. Only when the patient 12 is correctly positioned are the connections between the hook and loop strips 7 and the fleece sections 8 broken. For this purpose, the edge section is only slightly raised. This leads to an increase in the volume of the movement elements 5 (e.g., the described plastic foam or visco-foam parts 18), which then raise the edge sections 3 and mold to the contour of the body of the patient (see FIG. 5).

In the figures, each edge section 3 is shown as a continuous component that may be flexible over the length and breadth, so the edge section 3 may be easily adjusted to the shape of the body. In one embodiment, as shown by the broken lines 13 in FIG. 1, the respective edge sections 3 may be divided into a plurality of individual section elements that may be moved separately. A separate movement element may then be allocated to each section element, and this moves the section element.

FIGS. 1-5 show, as a movement element, a foam component that increases its volume. In other words, the foam component is an elastically deformable movement element. Instead of a foam material, a movement element in the form of a hollow body that may be elastically deformed and may be made in a wedge shape may be used. The hollow body is similarly deformable, but returns itself to the initial wedge shape.

Figure 6:
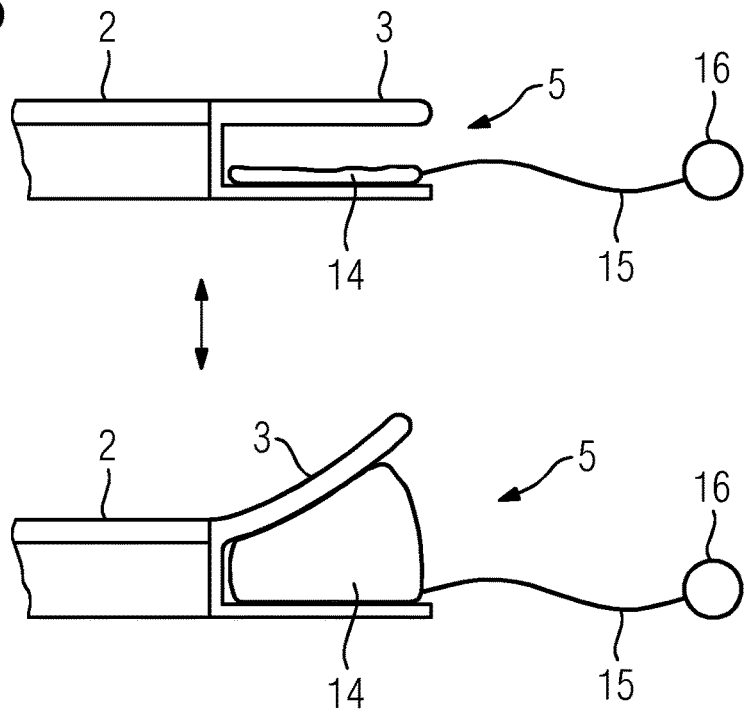
FIG. 6 shows a further embodiment of a body coil with inflatable cushions in a schematic diagram.

FIG. 6, by contrast, shows an alternative embodiment of a movement element 5 that is configured as an inflatable cushion 14. The inflatable cushion 14 is connected by a wire 15 to a pump 16. In the second illustration in FIG. 6, the cushion 14 is inflated. This also has a wedge shape, and this may be easily achieved by way of example in that the cushion 14 is made from PTFE (e.g., from a plastic that may be inflated in a stable form). The edge section 3 is also pivoted upwards relative to the middle section 2.

Figure 7:
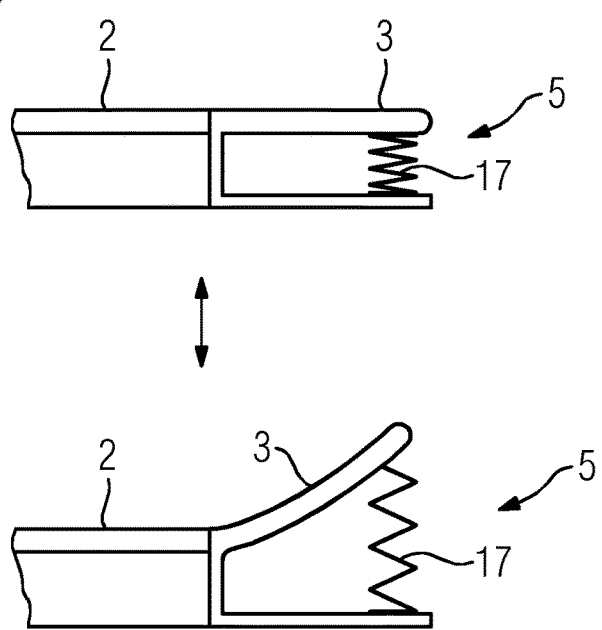
FIG. 7 shows a further embodiment of a body coil with spring elements.

FIG. 7 shows a further embodiment of a movement element 5 that is configured as a spring element 17 and is made from a suitable rubber-elastic material. The movement element 5 may likewise be fixed in a compressed form, from which the movement element 5 pivots the edge section 3 upwards after the pressure is relieved (see second diagram in FIG. 7).

Although the invention has been illustrated and described in detail by the exemplary embodiments, the invention is not restricted by the disclosed examples, and the person skilled in the art may derive other variations herefrom without departing from the scope of the invention.

While the present invention has been described above by reference to various embodiments, it should be understood that many changes and modifications can be made to the described embodiments. It is therefore intended that the foregoing description be regarded as illustrative rather than limiting, and that it be understood that all equivalents and/or combinations of embodiments are intended to be included in this description.

The invention claimed is:

1. A body coil comprising:
   a middle section;
   two opposing edge sections connected to sides of the middle section, respectively;

one or more coil elements incorporated in a shell material; and movement elements arranged beneath the two opposing edge sections, a first subset of the movement elements and a second subset of the movement elements operable to expand, the first subset of expandable movement elements pressing against a first edge section of the two opposing edge sections from beneath the first edge section, pressing against a first rigid surface opposite the first edge section from above the first rigid surface, and pivoting the first edge section relative to the middle section when the first subset of the movement elements expands, the second subset of expandable movement elements pressing against a second edge section of the two opposing edge sections from beneath the second edge section, pressing against a second rigid surface opposite the second edge section from above the second rigid surface, and pivoting the second edge section relative to the middle section when the second subset of the movement elements expands, wherein the body coil has a rectangular basic shape, and wherein the two opposing edge sections are pivotable along one pivot axis, respectively, relative to the middle section.

2. The body coil as claimed in claim 1, wherein the body coil is for magnetic resonance imaging.

3. The body coil as claimed in claim 1, wherein the movement elements are constructed as inflatable cushions or balloons.

4. The body coil as claimed in claim 1, wherein each edge section of the two opposing edge sections is divided into a plurality of individual, separately pivotal section elements, to which one of the movement elements, respectively, is allocated.

5. The body coil as claimed in claim 1, wherein pocket-like receptacles are provided on the two opposing edge sections, the pocket-like receptacles being operable for detachably receiving one or more of the movement elements.

6. The body coil as claimed in claim 1, wherein a first top edge of the middle section is flush with a top edge of one edge section of the two opposing edge sections, and a second top edge of the middle section is flush with a top edge of the other edge section of the two opposing edge sections.

7. The body coil as claimed in claim 1, wherein the movement elements are elastically deformable.

8. The body coil as claimed in claim 7, wherein for pivoting, the movement elements are operable to change a shape of the movement elements, starting from a compressed shape to an expanded shape.

9. The body coil as claimed in claim 8, wherein the movement elements are made from a rubber-elastic plastics material that serves as a spring element.

10. The body coil as claimed in claim 7, wherein each edge section of the two opposing edge sections is flexible, and
wherein one or more individual movement elements of the movement elements are provided along the respective edge section.

11. The body coil as claimed in claim 10, wherein the one or more movement elements arranged along the respective edge section have different elastic properties, different shapes, or different elastic properties and different shapes.

12. The body coil as claimed in claim 7, wherein for pivoting, the movement elements are operable to change volumes of the movement elements, respectively, starting from a compressed state to an expanded state.

13. The body coil as claimed in claim 12, wherein the movement elements are made from a plastic foam.

14. The body coil as claimed in claim 13, wherein the plastic foam is a visco-foam.

15. The body coil as claimed in claim 12, wherein the movement elements have a wedge shape in a relieved state.

16. The body coil as claimed in claim 12, wherein the movement elements are made from a non-foamed plastics material.

17. The body coil as claimed in claim 16, wherein the movement elements are constructed as hollow bodies.

18. An examination table comprising:
a top surface component with a rectangular indentation provided on an upper side of the top surface component; and
at least one body coil that is insertable into the rectangular indentation, each body coil of the at least one body coil comprising: a middle section;
two opposing edge sections connected to sides of the middle section, respectively;
one or more coil elements incorporated in a shell material; and
movement elements arranged beneath the two opposing edge section, a first subset of the movement and a second subset of the movement elements operable to expand, the first subset of expandable movement elements pressing against a first edge section of the two opposing edge sections from beneath the first edge section, pressing against a first rigid surface opposite the first edge section from above the first rigid surface, and pivoting the first edge section relative to the middle section when the first subset of the movement elements expands, the second subset of expandable movement elements pressing against a second edge section of the two opposing edge sections from beneath the second edge section, pressing against a second rigid surface opposite the second edge section from above the second rigid surface, and pivoting the second edge section relative to the middle section when the second subset of the movement elements expands, wherein the body coil has a rectangular basic shape, and wherein the two opposing edge sections are pivotable along one pivot axis, respectively, relative to the middle section.

19. The examination table as claimed in claim 18, wherein the movement elements are elastically deformable.

20. The examination table as claimed in claim 18, further comprising:
one or more securing devices provided on the top surface component at two opposing edges of the top surface component; and
holders provided on the body coil,
wherein the one or more securing devices are operable to secure the holders, and
wherein when secured, the one or more securing devices are operable to hold the two opposing edge sections of the body coil by compressing the respective movement elements in a position parallel to the middle section.

21. The examination table as claimed in claim 20, wherein the holders comprise hook and loop strips, and the one or more securing devices comprise fleece sections.

* * * * *